(12) United States Patent
Hembre et al.

(10) Patent No.: US 7,002,049 B2
(45) Date of Patent: Feb. 21, 2006

(54) PROCESS FOR α,β-DIHYDROXYALKENES AND DERIVATIVES

(75) Inventors: Robert Thomas Hembre, Johnson City, TN (US); Jonathan Michael Penney, Greenville, NC (US)

(73) Assignee: Eastman Chemical Company, Kingsport, TN (US)

( * ) Notice: Subject to any disclaimer, the term of this patent is extended or adjusted under 35 U.S.C. 154(b) by 190 days.

(21) Appl. No.: 10/453,705

(22) Filed: Jun. 3, 2003

(65) Prior Publication Data

US 2004/0044229 A1    Mar. 4, 2004

Related U.S. Application Data

(60) Provisional application No. 60/404,453, filed on Aug. 19, 2002.

(51) Int. Cl.
C07C 29/32    (2006.01)
(52) U.S. Cl. .................................................... 568/857
(58) Field of Classification Search ................ 568/857
See application file for complete search history.

(56) References Cited

U.S. PATENT DOCUMENTS

| | | | |
|---|---|---|---|
| 2,561,984 A | | 7/1951 | Hillyer et al. |
| 3,070,633 A | | 12/1962 | Utne et al. |
| 4,727,215 A | | 2/1988 | Schrock |
| 4,897,498 A | | 1/1990 | Monnier et al. |
| 5,087,710 A | | 2/1992 | Schrock et al. |
| 5,142,073 A | | 8/1992 | Schrock et al. |
| 5,146,033 A | | 9/1992 | Schrock et al. |
| 5,312,940 A | | 5/1994 | Grubbs et al. |
| 5,336,815 A | * | 8/1994 | Becker et al. ............... 568/857 |
| 5,342,909 A | | 8/1994 | Grubbs et al. |
| 5,342,985 A | | 8/1994 | Herrmann et al. |
| 5,445,963 A | | 8/1995 | Boaz |
| 5,750,815 A | | 5/1998 | Grubbs et al. |
| 5,831,108 A | | 11/1998 | Grubbs et al. |
| 5,889,128 A | | 3/1999 | Schrock et al. |
| 5,922,863 A | | 7/1999 | Grubbs et al. |
| 5,952,533 A | | 9/1999 | Fischer et al. |
| 5,969,170 A | | 10/1999 | Grubbs et al. |
| 6,172,182 B1 | | 1/2001 | Meurs et al. |
| 6,306,988 B1 | | 10/2001 | Grubbs et al. |
| 6,414,097 B1 | | 7/2002 | Grubbs et al. |
| 2002/0058812 A1 | | 5/2002 | Grubbs et al. |
| 2002/0058831 A1 | | 5/2002 | Wagener et al. |
| 2002/0137978 A1 | | 9/2002 | Grubbs et al. |

FOREIGN PATENT DOCUMENTS

| | | |
|---|---|---|
| DE | 40 09 910 A1 | 10/1991 |
| EP | 0 373 488 B1 | 5/1993 |
| EP | 1 022 282 A2 | 7/2002 |
| WO | WO 91/14665 | 10/1991 |
| WO | WO 93/20111 | 10/1993 |
| WO | WO 99/51344 | 10/1999 |
| WO | WO 02/00590 | 1/2002 |

OTHER PUBLICATIONS

Stumpf et al. *J. Chem. Soc., Chem. Commun.* 1995, 1127-1128.
Oguri et al. *Tetrahedron Letters 40*, 1999, 5405-5408.
Schwab et al. *J. Am. Chem. Soc.* 1996, 118, 100-110.
Hillmyer et al. *Macromolecules* 1997, 30, 718-721.
Valenti et al. *Macromolecules* 1998, 31, 2764-2773.
Wagener et al. *Macromolecules* 1997, 30, 7363-7369.
Barry et al. *Tetrahedron Letters.* 1983, 24, 661-664.
Denton et al. *Chimica Oggi* 1996, 17-18.
Thomas Ziegler et al *Tetrahedron: Asymmetry* 9, 1998, 765-780.
Tokunaga et al. *Science*, 277, 1997, 936-38.
E. F. L. J. Anet, *Aust. J. Chem.*, 19, 1966, 1677-1681.
Tan et al., *Inorg. Chem.* 1998, 37, 467-472.
J. Kuszmann et al., *Carbohydrate Research*,83, 1980, 63-72.
Xu. et al. *J. Am. Chem. Soc.*, 1992, 114, 7570-7571.
Fu et al., *J. Am. Chem. Soc.*, 1993, 115, 9856-9857.
Toste et al. *Pure and Applied Chemistry*, 2002, 74, 7-10.
Shrock, *Tetrahedron* 55,1999, 8141-8153.
Grubbs et al. *Tetrahedron* 54, 1998, 4413-4450.
Weskamp et al., *Ang. Chem. Intl. Ed. Engl.* 1998, 37, 2490-2493.
Bäckvall et al., *Tetrahedron Letters*, vol. 21, 1980, 4985-4988.
Kruper et al., *J. Org. Chem.* 1995, 60, 725-727.
Paddock et al., *J. Am. Chem. Soc.* 2001, 123, 11498-11499.
Kihara et al., *J. Org. Chem.* 1993, 58, 6198-6202.
Tu et al., *Journal of Catalysis*, 199, 2001, 85-91.

(Continued)

*Primary Examiner*—Fiona T. Powers
(74) *Attorney, Agent, or Firm*—Eric D. Middlemas; Bernard J. Graves, Jr.

(57) ABSTRACT

Disclosed is a process wherein a first olefin selected from certain α,β-dihydroxyalkenes and 4-(alkenyl)ethylenecarbonates is reacted with a second olefin reactant to produce an olefin metathesis product. When the first olefin reactant is an optically enriched or enantiomerically pure α,β-dihydroxyalkene, cross metathesis reactions produce products possessing the same optical purity. The α,β-dihydroxyalkenes and the 4-(alkenyl)ethylene carbonates may be converted to hydrogenated products, and the 4-(alkenyl)ethylenecarbonates may be decarboxylated to provide the corresponding epoxides. The products of the disclosure may be used as monomers for the preparation of specialty polyesters and as intermediates in the manufacture pharmaceuticals and other chemicals.

22 Claims, No Drawings

OTHER PUBLICATIONS

Banks, R.L., *Catalysis*, vol. 4, pp. 100-129.
Grubbs, Robert H., *Progress in Inorganic Chemistry*, vol. 24, 1-50.
Mol, Joannes C., *Catalysis Today* 51, 1999, 289-299.
Parshall et al., *Homogeneous Catalysis*, 2nd Ed., 217-236.
Cossy et al., *Journal of Organometallic Chemistry*, 624, 2001, 327-332.
Cossy et al., *Journal of Organometallic Chemistry*, 634, 2001, 216-221.
Morita et al., *Macromolecules*, 2000, 33, 6621-6623.
Ahmed et al., *Tetrahedron*, 55, 1999, 3219-3232.
Hillmyer et al., *Macromolecules*, 1995, 28, 8662-8667.
Maishal et al., *Tetrahedron Letters*, 43, 2002, 2263-2267.
Valenti et al., *ACS Polymer Preprints*, 1996, 32,2, 325-326.
Shrock, Richard R., *Tetrahedron* 55, 1999, 8141-8153.
Rutjes et al., *CHIMICA OGGI*, Jul./Aug., 1998, 21-24.

* cited by examiner

PROCESS FOR α,β-DIHYDROXYALKENES AND DERIVATIVES

This application claims the benefit under 35 U.S.C. §119 (e) of U.S. Provisional Application Ser. No. 60/404,453 filed Aug. 19, 2002, the disclosure of which is incorporated herein by reference.

FIELD OF THE INVENTION

This invention pertains to a process for the preparation of α,β-dihydroxyalkenes and derivatives thereof. More specifically, this invention pertains to a process for the preparation of α,β-dihydroxyalkenes and 4-(alkenyl)ethylenecarbonates by a metathesis reaction of a first olefin selected from certain α,β-dihydroxyalkenes and 4-(alkenyl)ethylenecarbonates with a second olefin reactant.

BACKGROUND OF THE INVENTION

Dihydroxyalkenes are useful starting materials for numerous industrial chemical products including pharmaceuticals, agrochemicals, coatings, epoxyresins, and polyesters. For example, enantiomerically pure α,β-dihydroxyalkenes are useful intermediates for stereoselective transformations leading to pharmaceutically active materials such as HIV protease inhibitors and cyclosporins (see, for example, Ziegler et al. *Tetrahedron: Asymmetry* 1998, 9, 765). Dihydroxyalkenes also may be used to prepare epoxyolefins, such as 3,4-epoxy-1-butene, through a cyclodehydration reaction. Epoxyolefins have a rich chemistry and can further converted into a wide range of commercially valuable chemicals such as furans, alkylidene carbonates, cyclopropyl compounds, cyclobutyl derivatives, epoxyalkanes, and lactones (see, for example, *Chimica Oggi*, May 1996, pp. 17–18). Although 3,4-epoxy-1-butene is readily available though the direct oxidation of butadiene, the preparation of other epoxyolefins is difficult and generally requires multiple processing steps and expensive reagents.

The existing preparative methods for α,β-dihydroxyalkenes typically involve direct dihydroxylation of a diene. For example, Sharpless et al. *J. Am. Chem. Soc.* 1992, 114, 7570, report the asymmetric dihydroxylation of dienes using 3 molar equivalents of $K_3Fe(CN)_6$ as the oxidant in the presence of 1,4-bis(9-O-dihydroquinidinyl)phthalazine. Although yields and enantioselectivity were high, this process requires expensive and toxic reagents and exhibits poor selectivity between the olefinic groups of the diene. Alternatively, α,β-dihydroxyalkenes may be prepared by the epoxidation of dienes with hydrogen peroxide (see, for example, Espenson et al. *Inorg. Chem.* 1998, 37, 467) in the presence of a transition metal catalyst. The epoxyalkene is then hydrolyzed to produce the corresponding α,β-dihydroxyalkene. These processes often require multiple processing steps to obtain pure products and require the use of hydrogen peroxide which can be hazardous on a commercial scale. In addition, it is inherent in the above procedures that the starting diene possess the the functional groups and structural features of the desired α,β-dihydroxyalkene products; thus, the preparation of the starting dienes is often difficult and expensive and limits the utility of these processes for the preparation of α,β-dihydroxyalkenes with a variety of structures.

Enantiomerically enriched alkanediols also may be prepared by kinetic resolution methods involving hydrolysis of the corresponding epoxides in a method described by Jacobsen et al. *Science* 1997, 277, 936 or by hydrolysis of diol esters described in U.S. Pat. No. 5,445,963. Although such techniques provide a diol with high enantiomeric purity, overall yields are inherently limited to the amount of the desired stereoisomer present in the starting epoxide or ester, i.e., about 50% in a racemic mixture. Such low yields often make these processes uneconomical for commercial applications.

Olefin metathesis could potentially provide useful new α,β-dihydroxyalkenes and derivatives, such as epoxyolefins and carbonates, using an inexpensive and available α,β-dihydroxyalkene, such as 3-butene-1,2-diol as a starting material. Traditional olefin methathesis processes, however, suffer from the disadvantage that olefins bearing functional groups, such as epoxy, amino, aldehydo, and hydroxyl rapidly deactivate the sensitive and expensive metathesis catalysts. For example, U.S. Pat. No. 5,952,533 discloses the metathesis of 3,4-epoxy-1-butene to give a bis-epoxy-olefin in less than 5% yields.

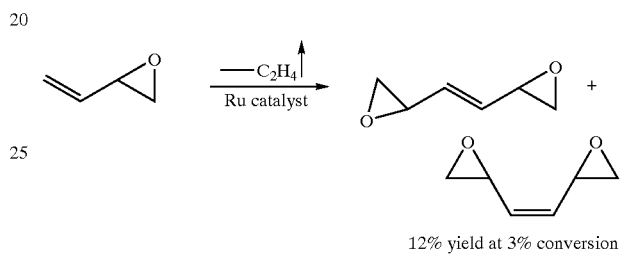

12% yield at 3% conversion

This problem restricts the use of the metathesis reaction to the preparation of relatively simple olefins with limited commercial applications.

During the past several years, olefin metathesis catalysts with increased tolerance to highly functionalized olefins, including carbohydrates and amino acids, have been described in PCT Application No. 02/00590, European Patent No. 1 022 282 A2; U.S. Pat. Nos. 6,306,988; 5,922,863; 5,831,108; and 4,727,215; U.S. patent application Ser. Nos. 09/849,100 and 09/891,144; Grubbs et al. *Pure and Applied Chemistry* 2002, 74, 7; Schrock et al. *Tetrahedron* 1999, 55, 8141; Herrmann et al. *Ang. Chem. Intl. Ed. Engl.* 1998, 37, 2490, and Grubbs et al. *Tetrahedron* 1998, 54, 4413. Although these catalysts show an increased tolerance toward various functional groups, hydroxyl groups in close proximity, for example adjacent or α- to the olefin, are reported to exhibit a strong retarding effect on catalyst activity (see, for example, Wagener et al. *Macromolecules* 1997, 30, 7363). To help counteract this retarding effect, protecting groups such as ethers and esters, frequently are attached to the hydroxyl groups prior to the metathesis step (see, for example, Hirama et al. *Tetrahedron Letters* 1999, 40, 5405). This approach, however, is unpredictable and highly dependent on the structure of the olefin and on the protecting group, (see, for example, Sarkar et al. *Tetrahedron Letters* 2002, 43, 2263). Even when such protecting groups are employed, the metathesis reaction often proceeds slowly and requires large amounts of catalyst for the reaction to proceed at practicable rates. Furthermore, the additional processing steps required to add and remove these protecting groups adds to the cost of the process and reduces product yields.

Thus, it is evident from the above that need exists for a flexible, efficient, and economical process for the preparation of α,β-dihydroxyalkenes either as racemic mixtures or as enantiomerically enriched products. It also would be desirable to use an olefin metathesis process which utilizes a simple, inexpensive, and readily available α,β-dihydroxyalkene or derivative thereof as a starting material. Finally, it would be desirable to convert the α,β-dihydroxyalkene products to the corresponding epoxyalkenes and alkanes and thus utilize the extensive chemistry and reactivity of the epoxide group for the preparation of pharmaceutical compounds, adhesives, and coatings.

SUMMARY OF THE INVENTION

We have unexpectedly discovered that α,β-dihydroxyalkenes and 4-(alkenyl)-ethylene carbonates react smoothly and at high rates with a second olefin reactant in the presence of olefin metathesis catalysts to give α,β-dihydroxyalkenes and 4-(alkenyl)ethylene carbonates with additional substituents in good yields. Thus, the present invention provides a process for the preparation of a compound having the formula:

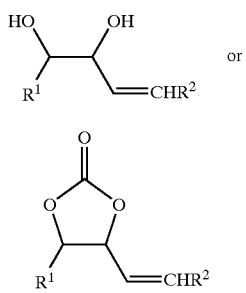
(I)

or (II)

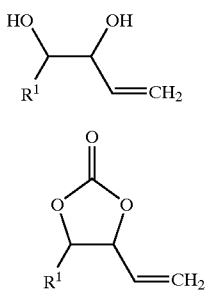

which comprises contacting a first olefin selected from α,β-dihydroxyalkenes and 4-(alkenyl)ethylenecarbonates having the formulas:

(III)

or (IV)

and at least one olefin having the formula $H_2C=CHR^2$ (V) or $R^2HC=CHR^2$ (VI) or a cycloalkene (VII) in the presence of an olefin metathesis catalyst under olefin metathesis conditions of pressure and temperature; wherein $R^1$ is hydrogen, a $C_1$ to $C_{10}$, substituted or unsubstituted, straight or branched chain alkyl radical; a $C_2$ to $C_{10}$, substituted or unsubstituted, straight or branched chain alkenyl radical; a $C_3$ to $C_{10}$, substituted or unsubstituted cycloalkyl or cycloalkenyl radical; a $C_6$ to $C_{10}$, substituted or unsubstituted aryl radical; or a $C_4$ to $C_{10}$, substituted or unsubstituted heterocylic radical containing from 1 to 3 heteroatoms selected from oxygen and sulfur; $R^2$ each is $C_1$ to $C_{10}$, substituted or unsubstituted, straight or branched chain alkyl radical; $C_2$ to $C_{10}$, substituted or unsubstituted, straight or branched chain alkenyl radical; $C_3$ to $C_{10}$, substituted or unsubstituted cycloalkyl or cycloalkenyl radical; $C_6$ to $C_{10}$, substituted or unsubstituted aryl radical; or $C_4$ to $C_{10}$, substituted or unsubstituted heterocylic radical containing from 1 to 3 heteroatoms selected from oxygen and sulfur; and cycloalkene (VII) is selected from the group consisting of substituted or unsubstituted cyclobutenes, cyclopentenes, cyclopentadienes, cyclohexenes, cycloheptenes, and cyclooctenes.

When reactant (III) or (IV) is an optically enriched α,β-dihydroxyalkene or 4-(alkenyl)ethylene carbonate, our process gives products possessing the same, or substantially the same, optical purity. Thus, a second embodiment of the present invention is a process for the preparation of an enantiomerically enriched compounds having the formulas:

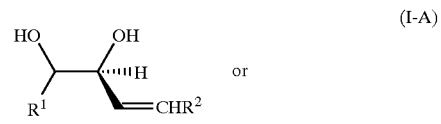
(I-A)

or (I-B)

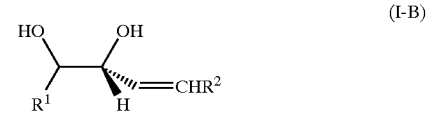

(II-A)

or

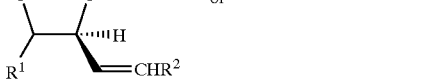

(II-B)

which comprises contacting an enantiomerically enriched α,β-dihydroxyalkene having the formula:

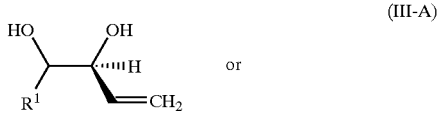
(III-A)

or (III-B)

(IV-A)

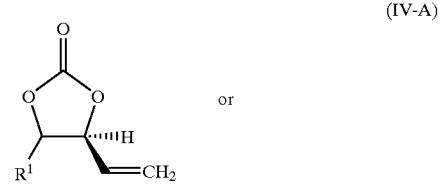

or

-continued (IV-B)

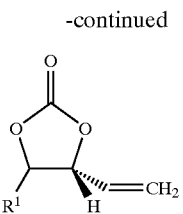

and at least one olefin having the formula H$_2$C=CHR$^2$ (V) or R$^2$HC=CHR$^2$ (VI) or a cycloalkene (VII) in the presence of an olefin metathesis catalyst under olefin metathesis conditions of pressure and temperature; wherein R$^1$, R$^2$, and cycloalkene (VII) are as defined above. Products (I-A) or (I-B) from the present invention have substantially the same enantiomeric purity of the corresponding reactant (III-A) or (III-B).

The present invention also provides a process in which compounds I, I-A, I-B, II, II-A, and II-B may be further hydrogenated to give products in which the alkenyl group is hydrogenated to a saturated alkyl group. If chiral or enantiomerically enriched compounds used as reactants, then the hydrogenated products retain the enantiomeric composition of the reactants.

Another embodiment of our invention is a process wherein the alkylene carbonates II, II-A, and II-B and their hydrogenation products may be decarboxylated to produce the corresponding epoxides. Our novel decarboxylation process offers higher yields of epoxides over a direct cross-metathesis route because of the tendency of the epoxide group to undergo side reactions under cross-metathesis conditions and to deactivate the metathesis catalyst.

DETAILED DESCRIPTION OF THE INVENTION

The present invention provides a process for the preparation of compounds having the formula:

(I)

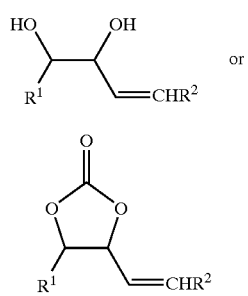

or (II)

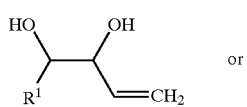

which comprises contacting a first olefin selected from α,β-dihydroxyalkenes and 4-(alkenyl)ethylene carbonates having the formula:

(III)

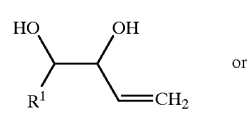

or

-continued (IV)

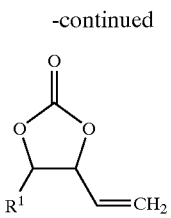

and at least one olefin having the formula H$_2$C=CHR$^2$ (V) or R$^2$HC=CHR$^2$ (VI) or a cycloalkene (VII) in the presence of an olefin metathesis catalyst under olefin metathesis conditions of pressure and temperature in the presence of an olefin metathesis catalyst, preferably a ruthenium-alkylidene complex. When the first olefin reactant is an enantiomerically enriched or pure α,β-dihydroxyalkene or 4-(alkenyl) ethylene carbonate, the process of the instant invention gives products possessing substantially the same enantiomeric purity. The terms "α,β-dihydroxyalkene" or "dihydroxyalkenes" as used herein are synonymous and are defined as any organic compound containing 2 adjacent hydroxyl groups or a diol group located adjacent or α to a carbon-carbon double bond. The products (I) and (II) may be hydrogenated to produce their saturated counterparts, α,β-dihydroxyalkanes or 4-(alkanyl)ethylene carbonates and, if (I) and (II) are enantiomerically enriched, the α,β-dihydroxyalkane or 4-(alkanyl)ethylene carbonate products retain the enantiomeric composition of the reactants. The two-step metathesis/hydrogenation sequence thus provides a unique pathway to chiral 1,2-alkanediols. In addition, our invention provides a process for 4-(alkenyl)ethylene carbonates and 4-alkylethylene carbonates that can be decarboxylated to produce their epoxide counterparts. The epoxides thus produced also retain the enantiomeric composition of the carbonate reactants. Thus, the two-step metathesis/decarboxylation sequence yields chiral epoxyalkenes and the three-step metathesis/hydrogenation/decarboxylation sequence yields chiral epoxides from enantiomerically enriched or pure 4-(alkenyl)ethylene carbonates. The α,β-dihydroxyalkenes may be used as monomers for the preparation of specialty polyesters, coatings, synthetic lubricants, and as intermediates in the manufacture of fine chemicals; epoxides derived from 4-(alkenyl)ethylene carbonate products are widely used in epoxy resins and optically pure or enriched derivatives find widespread application as biologically active molecules in the pharmaceutical and agricultural industries.

The process of the present invention utilizes a first olefin represented by the formula:

(III)

HO  OH

R$^1$   =CH$_2$ or (IV)

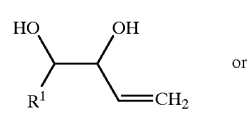

wherein R$^1$ represents hydrogen, a substituted or unsubstituted, straight or branched chain aliphatic radical containing 1 to 10 carbon atoms; a substituted or unsubstituted, straight or branched chain alkenyl radical containing 2 to 10 carbon atoms; a substituted or unsubstituted cycloalkyl or cycloalkenyl radical containing 3 to 10 carbon atoms; a substituted or unsubstituted aryl radical containing 6 to 10 carbon atoms, e.g., phenyl or napthyl; or a substituted or unsubstituted 4- and 10- membered heterocylic radical containing from 1 to 3 heteroatoms selected from oxygen and sulfur. The term "heterocyclic radical" denotes optionally substituted four to ten-membered rings that have 1 to 3 heteroatoms, selected independently from oxygen and sulfur. These three- to ten-membered rings may be saturated, partially unsaturated, or fully unsaturated.

The term "substituted" as used herein in conjunction with each of the above alkyl, alkenyl, cycloalkyl, cycloalkenyl, aryl, and heterocyclic radicals which may be represented by $R^1$ denotes the above radicals substituted with one or more halogen, $C_1$–$C_6$-alkyl, $C_1$–$C_6$-alkoxy, substituted $C_1$–$C_6$-alkyl, $C_1$–$C_6$-alkylthio, aryl, arylthio, aryloxy, $C_2$–$C_6$-alkoxycarbonyl, $C_2$–$C_6$-alkanoylamino, hydroxy, carboxyl, cycloalkoxy, nitro, keto, thioether, aldehydo, carboalkoxy, imido, sulfinato, sulfanato, sulfonamide, sulfoxy, phosphato, cycloalkyl, amino, mono-substituted amino, di-substituted amino, acyloxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkoxy, acyloxy, acyl, alkyl, alkoxy, aminoacyl, acylamino, azido, carboxyalkyl, cyano, heteroaryl, heteroaryloxy, heterocyclyl, heterocyclooxy, aminoacyloxy, oxyacylamino, thioalkoxy, substituted thioalkoxy, thioaryloxy, thioheteroaryloxy, trihalomethyl, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, or arylcarbonylamino groups.

Examples of substituted and unsubstituted alkyl and alkenyl radicals include, but are not limited to, methyl, ethyl, cyanomethyl, nitromethyl, hydroxymethyl, trityloxymethyl, propionyloxymethyl, aminomethyl, carboxymethyl, allyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, 6-hydroxyhexyl, 2,4-dichloro(n-butyl), 2-amino(iso-propyl), 2-carbamoyloxyethyl, n-propyl, isopropyl, isobutyl, n-butyl, tertiary butyl, pentyl, hexyl, 2-ethylhexyl, octyl, decyl, vinyl, 1-propenyl, 1-butenyl, 1-pentenyl, 2-octenyl, and various isomers thereof.

Examples of substituted and unsubstituted cycloalkyl and cycloalkenyl radicals include, but are not limited to, cyclopropyl, cyclobutyl, hydroxymethyl-cyclobutyl, cyclobutenyl, cyclopentyl, cyclopentenyl, cyclohexyl, cyclohexylcarbonyloxy, cyclohexenyl, cycloheptyl, 2-methylcyclopropyl, cycloheptenyl, 4-methylcyclohexyl, 3-methylcyclopentenyl, 4-(isopropyl)-cyclohexylethyl or 2-methyl-cyclopropylpentyl, and the like. Examples of heterocyclic radicals are tetrahydrofuranyl, tetrahydrothiofuranyl, thienyl, dioxanyl, pyranyl, furyl, chromenyl, xanthenyl, phenoxathiinyl, oxepane, oxathiolanyl, benzothienyl, and the like. Examples of substituted and unsubstituted aryl radicals are 4-chlorophenyl, 2,6-dichlorophenyl, 2,5-dichlorophenyl, 3,4-dichlorophenyl, 3-chlorophenyl, 3-bromophenyl, 4-bromoindenyl, 3,4-dibromophenyl, 3,4-dibromonaphthyl, 3-chloro-4-fluorophenyl, 2-fluorophenyl and the like; a mono- or di(hydroxy)aryl radical such as 4-hydroxyphenyl, 3-hydroxyphenyl, 2,4-dihydroxyphenyl, and the like; a nitroaryl group such as 3- or 4-nitrophenyl; a cyanoaryl group, for example, 4-cyanophenyl; a mono- or di(lower alkyl)aryl radical such as 4-methylphenyl, 2,4-dimethylphenyl, 2-methylnaphthyl, 4-(iso-propyl)phenyl, 4-ethylnaphthyl, 3-(n-propyl)phenyl and the like; a mono- or di(alkoxy)aryl radical, for example, 2,6-dimethoxyphenyl, 4-methoxyphenyl, 3-ethoxyindenyl, 4-(iso-propoxy)phenyl, 4-(t-butoxy)phenyl, 3-ethoxy-4-methoxyphenyl and the like; 3- or 4-trifluoromethylphenyl, a mono- or dicarboxyaryl radical such as 4-carboxyphenyl, 4-carboxynaphthyl; a mono- or di(hydroxymethyl)aryl radical such as 3,4-di(hydroxymethyl)phenyl, a mono- or di(aminomethyl) aryl radical such as 2-(aminomethyl)phenyl, or a mono- or di(methylsulfonylamino)aryl radical such as 3-(methylsulfonylamino)naphthyl. For the present process, it is preferred that $R^1$ is methyl, phenyl, or vinyl; however, it is especially preferred that $R^1$ is hydrogen.

Our process also utilizes a second olefin reactant having the formula $H_2C=CHR^2$ (V), or $R^2HC=CHR^2$ (VI), or a cycloalkene (VII) having 4 to 8 carbon atoms wherein $R^2$ is independently selected from the groups represented by $R^1$ except that $R^2$ is not hydrogen. Specific examples of olefin reactant (V) include, but are not limited to, propene, butene, pentene, hexene, octene, butadiene, isoprene, vinylcyclopropene, vinylcyclohexene or styrene. Non-limiting examples of olefin reactant (VI) include 2-butene, stilbene, and the like. Examples of cycloalkene (VII) include, but are not limited to, cyclobutene, cyclopentene, cyclooctene, norbornene, and cyclopentadiene, Preferably, the second olefin reactant is propene or butene.

The metathesis catalyst which may be used in the instant invention may be any heterogeneous or homogeneous transsistion metal compound which is effective for catalyzing metathesis reactions and is compatible with the functional groups present in the reactants. Preferred metathesis catalysts are heterogeneous or homogeneous compounds of transition metals selected from Groups 4 (IVA) and 6–10 (VIA-10) of the Periodic Table of the Elements. By the term "heterogeneous compound" it is meant any transition metal or metal compound of Groups 4 and 6–10 of the Periodic Table of the Elements admixed with, supported on, ion-exchanged with, deposited on, or coprecipitated with common inert support materials such as silica, alumina, silica-alumina, titania, zirconia, carbon, and the like. The support material also may be a acidic or basic macroreticulated ion-exchange resin. The term "homogeneous compound" means any Group 4 or Group 6–10 transition metal compound that is soluble or partly soluble in the reaction mixture. Effective metathesis catalysts may be prepared by methods well known to practitioners skilled in the art and are described in chemical journals such as Mol et al Catal. Today, 1999, 51, 289–99 and in PCT Application No. 02/00590; European Application No. 1 022 282 A2; and U.S. Pat. Nos. 5,922,863; 5,831,108; and 4,727,215; all of which are incorporated herein by reference.

The preferred olefin metathesis catalyst is a ruthenium or osmium alkylidene catalyst having the formula $MX_2[=CHR^3] L^1L^2$ wherein M is ruthenium or osmium, X is a halogen atom such as fluorine, chlorine, bromine, or iodine; or a pseudohalogen group such as a carboxylate or alkoxide; $R^3$ is independently selected from hydrogen or a hydrocarbon selected from the group consisting of $C_2$ to $C_{20}$ alkenyl, $C_2$ to $C_{20}$ alkynyl, $C_1$ to $C_{20}$ alkyl, aryl, $C_1$ to $C_{20}$ carboxylate, $C_2$ to $C_{20}$ alkoxy, $C_2$ to $C_{20}$ alkenyloxy, $C_2$ to $C_{20}$ alkynyloxy, aryloxy, $C_2$ to $C_{20}$ alkoxycarbonyl, $C_1$ to $C_{20}$ alkylthio, $C_1$ to $C_{20}$ alkylsulfonyl and $C_1$ to $C_{20}$ alkylsulfinyl, cycloalkyl, vinyl, or aralkyl; $L^1$ and $L^2$ are the same or different metal ligands selected from phosphines represented by the formula $P(R^4)_3$, wherein $R^4$ is alkyl, cycloalkyl, aryl, or aralkyl, for example, isopropyl, isobutyl, sec-butyl, neopentyl, neophyl, cyclopentyl or cyclohexyl; phosphites of the formula $P(OR^4)_3$, wherein $R^4$ is defined as above; or alkenes, cycloalkenes, alkynes, nitric oxide, imines, imidazoylidenes and dihydroimidazoylidenes. The term "pseudohalogen" as used herein is defined as any negatively charged, non-halogen, organic or inorganic compound which may coordinate to a metal or otherwise function as a metal ligand in a similar stoichiometry or manner to a halogen atom. Examples of pseudohalogens include carboxylates, amidates, thiocyanates, nitrates, alkoxides, benzoate, and sulfonates and the like. More specific examples of pseudohalogens include acetylacetonate, $C_1$ to $C_5$ carboxylate, $C_1$ to $C_5$ alkyl, phenoxy, $C_1$ to $C_5$ alkoxy, $C_1$ to $C_5$ alkylthio, aryl, and $C_1$ to $C_5$ alkyl sulfonate; each optionally substituted with $C_1$ to $C_5$ alkyl or a phenyl group optionally substituted with halogen, $C_1$ to $C_5$ alkyl or $C_1$ to $C_5$ alkoxy. The preferred catalysts are well known and described in detail in the patents listed above. Particularly preferred catalysts are commercially available and include benzylidene-bis-(tricyclohexylphosphine)ruthenium dichloride [M is ruthenium, X is Cl, $R^3$ is phenyl, and $L^1$ and $L^2$ are $P(Cy)_3$, Cy=cyclohexyl] and benzylidene-(tricyclohexylphosphine)[1,3-bis-(2,4,6-trimethylphenyl )-4,5dihydroimidazol-2-ylidene)ruthenium dichloride [in which, according to the formula above, M is ruthenium, X is Cl, $R^3$ is phenyl, and $L^1$ is $P(Cy)_3$, $L^2$ is represented by the formula below:]

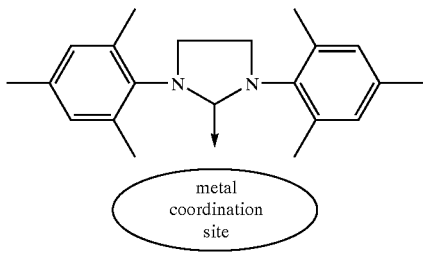

1,3-bis-(2,4,6-trimethylphenyl)-4,5-dihydroimidazol-2-ylidene

It is to be understood that the catalysts described above may be present within the reaction mixture as the structures described above or may be transformed into one or more different metal compounds or metal complexes during the course of the reaction through ligand exchange processes well known to persons skilled in the art or through the chemical processes related to with the operation of the catalyst.

Other similar catalysts have been prepared in situ by the combination of appropriate catalyst precursors. For instance a preferred catalyst precursor is of the formula $MX_2[Arene][P(R^4)_3]L^1$ wherein M is osmium or, preferably, ruthenium; X is a halogen such as bromine, iodine or, preferably, chlorine and $R^4$ is hydrogen, alkyl, cycloalkyl, aryl or aralkyl, preferably, cyclohexyl; $L^1$ is $P(R^4)_3$, imidazoylidene, or dihydroimidazoylidenes or, preferably, 1,3-bis-(2,4,6-trimethylphenyl)-4,5-dihydroimidazol-2-ylidene (as illustrated above); and arene is a 6-membered carbocyclic aromatic molecule which may carry 1 or more alkyl substituents such as benzene, toluene, xylene, cumene, and the like. A specific example of a useful catalyst precursor is $RuCl_2[p\text{-cumene}]P(Cy)_3/N_2CHSi(Me)_3$ wherein Ph is phenyl and Cy is cyclohexyl. Further examples are described by Noels et al., *J. Chem. Soc., Chem. Commun.* 1995, pp. 1127–1128.

More recent examples of in situ catalyst generation from catalyst precursors are disclosed in U.S. patent application Ser. No. 09/948,115 where $[\{(p\text{-cymene})RuCl_2\}_2]$ is combined with alkynes and imidazolylidene ligands such as that illustrated above. A specific example of such a combination is $[\{(p\text{-cymene})RuCl_2\}_2]$/t-butylacetylene/1,3-bis-(2,4,6-trimethylphenyl)-4,5-dihydroimidazole. The low cost, ready availability, and greater stability of these catalyst precursors make them attractive for commercial applications.

The process typically is carried out at a temperature in the range of about −10 to about 90° C., preferably at a temperature in the range of about 0 to about 70° C., or more preferably at a temperature in the range of about 0 to about 60° C. Pressure is not an important factor of the present process and, therefore, pressures above or below ambient pressure may be used as necessary to maintain the reaction mixture in the liquid phase or to prevent boiling of the reaction mixture, if desired. The process may be performed in the liquid or gas phase. If performed in the liquid phase, the process may be performed with or without an added solvent. Examples of solvents include hydrocarbons such as hexane, heptane, benzene, toluene and xylene; chlorinated hydrocarbons such as dichloromethane, dichloroethane, chlorobenzene and dichlorobenzene; ethers such as diethyl ether, diisopropyl ether, tetrahydrofuran, and methyl tert-butyl ether; and esters such as ethyl acetate, n-propyl acetate, and methyl butyrate.

The amount of the metathesis catalyst typically employed in the process may be in the range of about $10^{-5}$ to about 1 mole of catalyst per mole of reactant (III) or reactant (IV), preferably from about $10^{-4}$ mole to about $10^{-1}$ mole of catalyst per mole of reactant, and most preferably in a range of about $2\times10^{-4}$ to about $5\times10^{-2}$ mole of catalyst per mole of reactant (III) or reactant (IV).

The process of the present invention is preferably conducted under a substantially inert atmosphere. The term "inert" as used herein, means unreactive with any of the reactants, solvents, or other components of the reaction mixture under reaction conditions of temperature, time, and pressure. Such inert conditions are generally accomplished by using inert gas such as carbon dioxide, helium, nitrogen, argon, among other gases, to blanket or purge the reaction mixture often under slightly elevated pressures.

The present invention may be conducted under continuous, semicontinuous, and batch modes of operation and may utilize a variety of reactor types. Examples of suitable reactor types include, but are not limited to, stirred tank, continuous stirred tank, trickle bed, tower, slurry, and tubular reactors. The term "continuous" as used herein means a process wherein reactants are introduced and products withdrawn simultaneously in an uninterrupted manner. By "continuous" it is meant that the process is substantially or completely continuous in operation and is to be contrasted with a "batch" process. "Continuous" is not meant in any way to prohibit normal interruptions in the continuity of the process due to, for example, start-up, reactor maintenance, or scheduled shut down periods. The term "batch" process as used herein means a process wherein all the reactants are added to the reactor and then processed according to a predetermined course of reaction during which no material is fed or removed into the reactor. The term "semicontinuous" means a process where some of the reactants are charged at the beginning of the process and the remaining reactants are fed continuously as the reaction progresses. Alternatively, a semicontinuous process may also include a process similar to a batch process in which all the reactants are added at the beginning of the process except that one or more of the products are removed continuously as the reaction progresses.

The ethylene liberated during the reaction is preferably removed continuously from the reaction mixture. Ethylene can be purged out of the reactor using an inert gas such as methane, nitrogen, argon or carbon dioxide. It is preferred, however, to allow the liberated ethylene to exit the reactor through the release of excess reactor pressure.

The metathesis reaction is generally complete after a reaction time of from 0.5 to 48 hours. After completion of the reaction, the reaction products may be separated from the reaction mixture by several purification procedures well known to persons skilled in the art including, but not limited to crystallization, distillation, extraction, and the like. For example if the reaction products are volatile, the products may be separated by distillation from the reaction milieux. The metathesis catalyst will remain in the distillation bottoms and may, after work-up, be returned or recycled to the reaction.

The products provided by our novel process retain the enantiomeric composition of the reactants. Thus, enantiomerically enriched α,β-dihydroxyalkenes and 4-(alkenyl)ethylenecarbonates of the present invention may be used to prepare enantiomerically enriched compounds. The term "enantiomerically enriched" as use herein means one optical isomer or enantiomer is in excess of the opposite optical isomer or enantiomer. Thus another embodiment of the present invention is a process for the preparation of an enantiomerically enriched compound having the formula:

(I-A)

(I-B)

(II-A)

(II-B)

which comprises contacting an enantiomerically enriched α,β-dihydroxyalkene having the formula:

(III-A)

(III-B)

(IV-A)

(IV-B)

and at least one olefin having the formula $H_2C=CHR^2$ (V) or $R^2HC=CHR^2$ (VI) or a cycloalkene (VII) in the presence of an olefin metathesis catalyst wherein $R^1$, $R^2$, the cycloalkene (VII), and the metathesis catalyst are defined as described previously. In this embodiment, the products (I-A), (I-B), (II-A, and (II-B) have substantially the same enantiomeric composition of the corresponding reactant (III-A) or (III-B). The term "enantiomeric composition" means the relative concentration of dextrorotatory and levorotatory enantiomers in the reactants or in the products. Although the catalysts, solvents, process conditions of temperature and pressure, and purification methods described previously also may be used with enantiomerically enriched α,β-dihydroxyalkene and 4-(alkenyl)ethylene carbonate reactants, the preferred catalyst is a ruthenium phosphine catalyst having the formula $RuCl_2[=CHPh][P(Cy)_3]_2$ wherein Cy is cyclohexyl, and the preferred temperature is in the range of about 0 to about 60° C.

The products of our metathesis process, that is compounds I, I-A, I-B, II, II-A, or II-B, may be may be hydrogenated to convert the alkenyl group to a saturated, alkyl group to produce compounds VIII, VIII-A, VIII-B, XI, XI-A, or XI-B, respectively, that are represented by the the formulas:

(VIII)

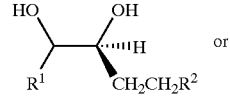
(VIII-A)

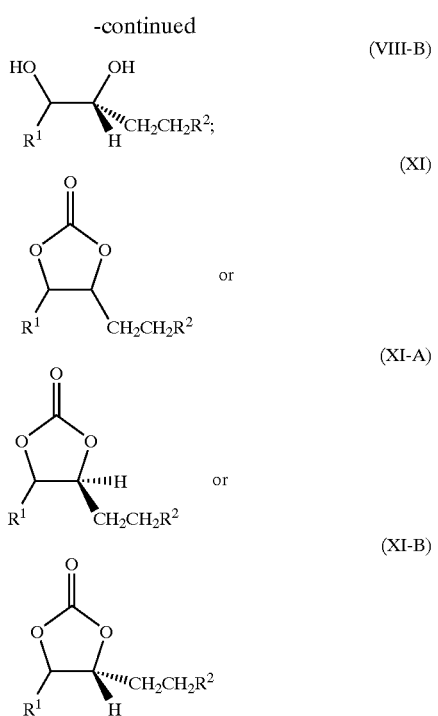

wherein $R^1$ and $R^2$ are defined as described hereinabove. If enantiomerically enriched olefins, e.g., compounds represented by formulas I-A, I-B, II-A, and II-B, are employed, the products VIII-A, VIII-B, XI-A, and XI-B retain sustantially the same enantiomeric composition of the reactants.

The hydrogenation may be carried out under mild conditions using a variety of procedures well known to persons skilled in the art. For example, if the metathesis catalyst is present therein in homogeneous form, the reaction mixture from the metathesis reaction may be hydrogenated directly with hydrogen without addition of a further hydrogenation catalyst, for example, as described in J. Am. Chem. Soc., 2001, 123, pp. 11312–11313. Alternatively, the products of the metathesis reaction may be separated by common, well known procedures such as distillation, extraction, crystallization, or other techniques familiar to skilled practitioners and subsequently hydrogenated in a separate reaction step using one or more catalysts effective for the hydrogenation of carbon-carbon double bonds. Non-limiting examples of hydrogenation catalysts include one or more metals or compounds of metals of Groups 7 to 11 of the Periodic Table of the Elements. These may be present in the form of elemental metal, metal oxides, metal sulphides, or as metal complexes with various organic ligands well known to those skilled in the art. The preferred catalysts may be used, for example, as supported catalysts, skeletal catalysts, black metal, mixed metal catalysts, or as metal complexes with phosphine ligands. Prior to use, the catalysts may be activated by heating in a hydrogen atmosphere. Further examples of hydrogenation catalysts are one or more catalysts selected from Pt black, Pt/C, Pt/$Al_2O_3$, $PtO_2$, Pd black, Pd/C, Pd/$Al_2O_3$, Pd/$SiO_2$, Pd/$CaCO_3$, Pd/$BaSO_4$, Rh/C, Rh/$Al_2O_3$, Ru/$SiO_2$, Ni/$SiO_2$, Raney nickel, Co/$SiO_2$, Co/$Al_2O_3$, Raney cobalt, Fe, Fe-containing mixed catalysts, Re black, Raney rhenium, Cu/$SiO_2$, Cu/$Al_2O_3$, Raney copper, Cu/C, $PtO_2$/$Rh_2O_3$, Pt/Pd/C, $CuCr_2O_4$, $BaCr_2O_4$, Ni/$Cr_2O_3$/$Al_2O_3$, $Re_2O_7$, CoS, NiS, $MOS_3$, Cu/$SiO_2$/$MoO_3$/$Al_2O_3$, and phosphine complexes of Ru, Rh, and Ir. The designation of a catalyst as "M/support" as used herein denotes a metal or metal compound deposited on, admixed with, inpregnated in, ion-exchanged with, coprecipitated with, or supported on a support material, such as carbon, silica, barium sulfate, alumina, chromia, and the like. Preferred hydrogenation catalysts include heterogeneous catalysts as described, for example, in Kropf, Methoden der Organischen Chemie, Houben-Weyl, Thieme Verlag 1980, vol. IV/1c, p. 16–44. Particularly preferred catalysts are one or more metals and/or metal compounds selected from Groups 7 to 11 of the Periodic Table of the Elements, for example, Pd/C, Pt/C, Re/C, Cu/C, Cu/$SiO_2$, Ni/C, Raney nickel, Raney cobalt, and phosphine complexes of metals from Groups 8 to 10 of the Periodic Table, with Pd/C being especially preferred.

The hydrogenation may be carried out at a hydrogen pressure in the range of from 1 to about 300 bars gauge ("barg"), preferably from about 1 to about 100 barg, or more preferably from about 1 to about 50 barg. The preferred reaction temperature is in the range of about 20 to about 300° C., more preferably from about 20 to about 200° C. and even more preferably from about 20 to about 150° C. In the event that the metathesis step of the process provides less than 100% conversion of the reactants, it is preferred to separate the unreacted olefin reactant by distillation, extraction, or crystallization prior to the hydrogenation step.

The hydrogenation step may carried out with or without a solvent. A variety of solvents may be used. Non-limiting examples of solvents which may be used in our process include water, alcohols, diols, esters, ethers, amides, sulfoxides, sulfones, nitriles, ketones, aldehydes, and mixtures thereof. Preferably, the solvent is an alcohol. Examples of alcohols which may be used as solvents include, but are not limited to, methanol, ethanol, propanol, n-butanol, isobutanol, isopropanol, 2-butanol, n-hexanol, octanol, and the various isomers thereof. The most preferred solvents are methanol and ethanol.

The hydrogenation step of the present invention includes continuous, semi-continuous, and batch modes of operation, as described hereinabove, and may utilize a variety of reactor types. Examples of suitable reactor types include, but are not limited to, stirred tank, continuous stirred tank, trickle bed, tower, slurry, tubular, and fluidized bed reactors. The preferred reactor types are stirred tank, continuous stirred tank, and trickle bed reactors.

The alkylene carbonate products of the present invention, that is compounds represented by the formulas II, II-A, II-B, XI, XI-A, and XI-B as described above, may be further reacted to give the corresponding epoxides represented by the formulas:

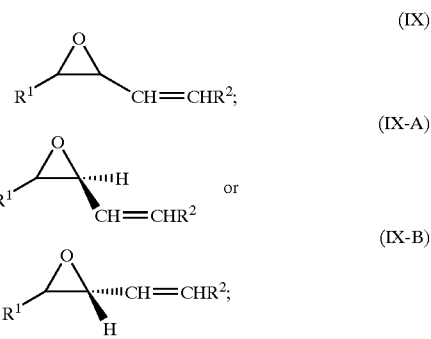

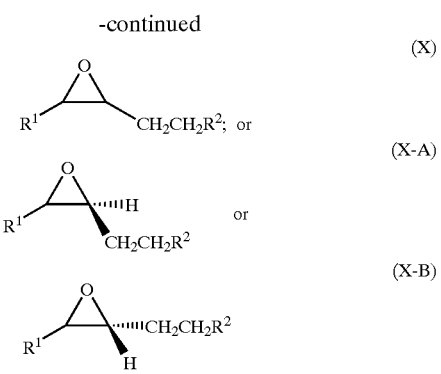

wherein $R^1$ and $R^2$ are defined as described hereinabove, by heating the carbonates in the presence of a decarboxylation catalyst. If enantiomerically enriched carbonates, e.g., compounds represented by formulas XI-A, and XI-B, are employed, the products, as represented by the formulas X-A and X-B, retain sustantially the same enantiomeric composition of the reactants.

The decarboxylation process may be carried out in a solvent in the presence of a decarboxylation catalyst. Halide anions are effective decarboxylation catalysts and thus a catalyst may be selected from lithium, sodium, potassium, rubidium or cesium salts of fluoride, chloride, bromide or iodide ions. Use of a solvent to favor the solubility of these salts or the addition of agents such as crown ethers to enhance the solvation of a salt in a given solvent may be used to increase their catalytic activity. For similar reasons, one or more ammonium or phosphonium salts of the halides may be used as decarboxylation catalysts. Preferably, the ammonium or phosphonium salts are liquids under process conditions of pressure and temperature. In this embodiment, the ammonium and/or phosponium salts are known as "ionic liquids" and can serve both as the reaction solvent and the decarboxylation catalyst. Because ionic liquids have very low vapor pressures, they can be a very effective catalyst/solvent medium for the production of relatively low-boiling epoxides, which are removed by fractionation as they are produced from their higher boiling carbonate precursors. Decarboxylation catalysts which may be used include, but are not limited to, tetraalkyl- or arylalkylphosphonium halides, tetraalkyl- or arylalkylammonium iodides, and alkali metal halides. Exemplary ammonium salts useful as decarboxylation catalysts include, but are not limited to, tetramethylammonium chloride, triethylmethylammonium chloride, trimethylbenyzlammonium chloride, triethylbenzylammonium chloride, tricaprylmethylammonium chloride (Aliquat 336), tetraethylammonium bromide, tetrabutylammonium bromide, tetrapentylammonium iodide, tetrahexylammonium acetate, tetraoctylammonium iodide, tetradecylammonium iodide, tetradodecylammonium iodide, tetrapropylammonium iodide, tetrabutylammonium iodide, trioctylammonium iodide, N-octylquinuclidinium iodide, N-octylquinuclidinium acetate, N,N'-dimethyl-N,N'-dihexadecylpiperazinium diiodide, dimethyl-hexadecyl-[3-pyrrolidinylpropyl]ammonium iodide; imidazolium halides include, but are not limited to, 1-ethyl-3-methylimidazolium chloride, 1-butyl-3-methylimidazolium chloride, 1-hexyl-3-methylimidazolium chloride, 1,3-dimethylimidazolium iodide; pyridinium halides include, but are not limited to, N-ethyl-pyridinium chloride, N-butyl-pyridinium chloride, N-hexyl-pyridinium chloride, N-octylpyridinium iodide, N-methyl-3,4-lutidinium iodide; phosphonium salts include, but are not limted to, tetrabutylphosphonium chloride, tributyl(tetradecyl )phosphonium chloride, tetrabutylphosphonium bromide, trioctyl(octadecyl)phosphonium iodide, tetraoctylphosphonium iodide, tetrabutylphosphonium iodide, triphenyl(hexyl)phosphonium iodide, triphenyl(octyl)-phosphonium iodide, tribenzyl(octyl)phosphonium iodide, tribenzyl(dodecyl)phosphonium iodide, triphenyl(decyl) phosphonium iodide, triphenyl(dodecyl)phosphonium iodide, tetrakis(2-methylpropyl)phosphonium iodide, tris(2-methylpropyl)(butyl)phosphonium iodide, triphenyl(3,3-dimethylbutyl)phosphonium iodide, triphenyl(3-methylbutyl)phosphonium iodide, tris(2-methylbutyl)(3-methylbutyl) phosphonium iodide, triphenyl[2-trimethylsilylethyl] phosphonium iodide, tris(p-chlorophenyl)(dodecyl) phosphonium iodide, hexyltris(2,4,6-trimethylphenyl) phosphonium iodide, tetradecyltris(2,4,6-trimethylphenyl) phosphonium iodide, dodecyltris(2,4,6-trimethylphenyl) phosphonium iodide, and the like. Preferred halide decarboxylation catalysts include cesium chloride, 1-butyl-3-methylimidazolium chloride, tributyl(tetradecyl)phosphonium chloride, and tetraethylammonium bromide.

Transition metal complexes may also serve as decarboxylation catalysts. Examples of such complexes are described in Tetrahedron Lett. 1980, 4985, J. Org. Chem. 1995, 60, 725, and J. Am. Chem. Soc. 2001, 123, 11498. The discussion and references therein are included here as evidence, but are not limiting, to the application of such catalysts in the instant invention.

Other investigators have found that psuedo-halide anions such as acetate, thiophenoxide, cyanide, and p-toluenesulfonate may be substituted for halide anions as decarboxylation catalysts for cyclic carbonates. Such alternative catalysts are discussed in J. Org.Chem. 1993, 58, 6198, and the references therein and are incorporated herein as exemplary.

The decarboxylation catalyst may be a heterogeneous catalyst in which case the decarboxylation may be carried out either in a slurry phase or at elevated temperature in the gas phase. Such processes and catalysts are illustrated in J. Catal. 2001, 199, 85. The selection of such catalysts depend on the physical properties, such as boiling points, of the reactant carbonate and product epoxide. In large volume, commercial applications such heterogeneous catalysts may be preferred. Non-limiting examples of heterogeneous decarboxylation catalysts include basic metal oxides, such as magnesium oxide and mixtures of magnesium and aluminum oxides as well as zeolites. Examples of other heterogeneous decarboxylation catalysts may be found in the text and references noted above and are incorporated herein by reference.

The decarboxyation step may be carried out continuously or batchwise. The preferred reaction temperature at a reaction temperature of from about 100° C. to about 300° C., preferably from about 120° C. to about 250° C. and more preferably from about 150° C. to about 200° C. The pressure of the decarboxylation step is not critical but is preferably maintained at or below ambient pressure. The preferred pressure is in the range of 0.001 barg to about 10 barg.

The decarboxylation process also may be carried out in the absence of or in a variety of solvents. Non-limiting examples of solvents which may be used in our process include water, alcohols, diols, esters, ethers, amides, sulfoxides, sulfones, nitrites, ketones, aldehydes, and mixtures thereof. Preferably, the solvent is a polar aprotic solvent such as N,N-dimethylformamide, dimethylsulfoxide, or sulfolane. More preferably the decarboxylation reaction may be conducted in the presence of an ionic liquid as described hereinabove. It is preferred, but not essential, to carry out the decarboxylation reaction such that the epoxide product is distilled from the reaction mixture as it is formed. In this embodiment, the preferred solvent is an ionic liquid, which also serves as a decarboxylation catalyst, and the preferred pressure is in the range of about 0.001 barg to about 1 barg.

The decarboxylation step of the present invention may be carried out continuous, semi-continuous, and batch modes of operation, as described above, and may utilize a variety of reactor types. Examples of suitable reactor types include, but are not limited to, stirred tank, continuous stirred tank, trickle bed, tower, slurry, fluidized bed, and tubular reactors. The preferred reactor type, however, is a stirred tank or continuous stirred tank reactor.

The process of the present invention is further illustrated by the following examples.

EXAMPLES

The catalyst used in the examples has the formula $Cl_2Ru=CHPh][P(Cy)_3]_2$ and was prepared following the procedures reported by Grubbs et al. *J. Am. Chem. Soc.* 1993, 115, 9856. Gas chromatography (Hewlett Packard 5890®) was carried out with flame ionization detection using a a fused-silica capillary column with a cross-linked, surface bonded modified polyethylene glycol stationary phase (25 m×0.25 mm, 0.25$\mu$ film) and a temperature program: 35° C. (2 min), +20°/min, 240° C. (2 min). Chiral GC analyses were carried out using thermal conductivity detection on a capillary column with a chiral stationary phase (CYCLOSILB® GC column; 10 m×0.25, 0.25$\mu$ film) and a temperature program: 40° C. (6 min), +70°/min, 120° C. (12 min). Using this method the two enantiomers of 1,2-dihydroxy-3-butene are observed at retention times of 10.96 and 11.14 min, corresponding to the S- and R-isomers, respectively. Reference samples of enantiopure (R)- and (S)-1,2-dihydroxy-3-butene were prepared and their absolute configuration determined by the methods described in U.S. Pat. No. 5,250,743. An enantiomeric excess of 94% was measured by this method for the sample of (R)-1,2-dihydroxy-3-butene used in the experiments below. $^1$H NMR spectra were obtained on a 300 MHz spectrometer with samples dissolved in d$_2$-dichloromethane or CDCl$_3$ using 1,3,5-trimethoxybenzene (TMB) as an internal standard. Chemical shifts ($\delta$) are referenced to residual protons in CHDCl$_2$ at 5.32 and CHCl$_3$ at 7.27 ppm.

Example 1

Cross-Metathesis of 1,2-dihydroxy-3-butene with 1-pentene. In a two-necked, 100 mL, round-bottom flask were placed 0.301 mL 1,2-dihydroxy-3-butene (0.315 g, 3.58 mmol), 3.92 mL of 1-pentene (2.51 g, 35.8 mmol), TMB (0.060 g, 0.36 mmol), and 10 mL CH$_2$Cl$_2$. A condenser and an addition funnel were attached and 60 mg (PCy$_3$)$_2$Cl$_2$Ru=CHPh (71.6 $\mu$mol, 2.0 mol percent) was added to the addition funnel. The entire system was degassed through three freeze-pump-thaw cycles, then the solution heated to reflux. Upon reaching reflux, 10 mL of degassed CH$_2$Cl$_2$ was added to the Cl$_2$Ru=CHPh[P(Cy$_3$)]$_2$ and the purple solution added all at once to the refluxing solution. A red-brown solution quickly formed which turned to orange over a 2 hour period. Samples (0.7 mL) were removed periodically for $^1$H NMR analysis. After 4 hours, 70% consumption of the 1,2-dihydroxy- 3-butene was observed along with formation of a single product, 1,2-dihydroxy-3-heptene, in quantitative yield as determined by integration relative to TMB. $^1$H NMR (CDCl$_3$) $\delta$ 5.75 (m, 1H), 5.42 (dd, 1H), 4.20 (m, 1H), 3.62 (dd, 1H), 3.45 (m, 1H), 2.00 (q, 2H), 1.40 (m, 2H), 0.90 (t, 3H).

Comparative Example 1

Self-metathesis of 1,2-dihydroxy-3-butene. 1,2-Dihydroxy-3-butene (158 mg, 1.8 mmol) and (PCy$_3$)$_2$Cl$_2$Ru=CHPh (30 mg, 0.036 mmol, 2.0 mol %) were dissolved in dry dichloromethane (5 ml). The solution was degassed then heated to reflux. Gradually, the solution's purple color changed to red-brown and a white solid formed. After 21 h heating was stopped and the white solid was filtered and dried in vacuo to give 11 mg, (0.074 mmol, 8.2% yield) of 3,4-dideoxyhexitol. $^1$H NMR (D$_2$O) $\delta$ 5.80 (s, 1H), 4.25 (br s, 1H), 3.62 (m, 1H), 3.52 (m, 1H).

Comparative Example 2

Self-metathesis of 2-hydroxy-3-butene. 2-Hydroxy-3-butene (129 mg, 1.8 mmol) and (PCy$_3$)$_2$Cl$_2$Ru=CHPh (30 mg, 0.036 mmol, 2.0 mol %) were dissolved in dry dichloromethane (5 ml). The solution was degassed then heated to reflux for 16 hours. 1H NMR of the sample suggested that 2-butanone was the sole product. This was confirmed by GC analysis vs. an authentic standard.

Comparative Example 3

Cross-Metathesis of allyl alcohol with 1-pentene. In a two-necked, 100 mL, round-bottom flask were placed 0.244 mL allyl alcohol (0.208 g, 3.58 mmol), 3.92 mL of 1-pentene (2.51 g, 35.8 mmol), trimethoxybenzene (TMB, 0.060 g, 0.36 mmol), and 10 mL CH$_2$Cl$_2$. A condenser and an addition funnel were attached and 60 mg (PCy$_3$)$_2$Cl$_2$Ru=CHPh (71.6 $\mu$mol, 2.0 mol percent) was added to the addition funnel. The entire system was degassed through 3 freeze-pump-thaw cycles, then the solution heated to reflux. Upon reaching reflux, 10 mL of degassed CH$_2$Cl$_2$ was added to the Cl$_2$Ru=CHPh[P(Cy$_3$)]$_2$ and the purple solution added all at once to the refluxing solution. A red-brown solution formed which turned to yellow within one hour. After two hours $^1$H NMR analysis shows only a very small amount of cross metathesis product (3.5% yield vs. int. std. TMB) and no remaining allyl alcohol. Propionaldehyde was formed in 18% yield along with a series of unidentified minor products.

Example 2

Cross-Metathesis of 1,2-dihydroxy-3-butene with propylene. Racemic 1,2-dihydroxy-3-butene (158 mg, 1.8 mmol) and Cl$_2$Ru=CHPh[P(Cy$_3$)]$_2$ (30 mg, 0.036 mmol, 2.0 mol %) were placed in a 150 mL glass pressure bottle (Fisher-Porter® reaction flask) and dissolved in dry dichloromethane (5 mL). The solution was degassed, pressurized with 50 psig of propylene and heated to 45° C. After 15 hours, heating was stopped and the pressure released. Reactants and products were analyzed using the chiral capillary GC method described above. Two pairs of peaks of equal intensity with retention times of 10.82 and 10.95 minutes in the first pair and 11.58 and 11.96 minutes in the second pair and an integration ratio of 10.4:1.0 were assigned to a corresponding mixture of trans- and cis-1,2-dihydroxy-3-pentene enantiomers, respectively. $^1$H NMR (CDCl$_3$) $\delta$ 5.80 (m, 1H), 5.45 (dd, J=15.0, 6.4 Hz; 1H), 4.20 (m, 1H), 3.62 (dd, 1H), 3.48 (m, 1H), 1.72 (d, 3H).

Example 3

Cross-metathesis of (R)-1,2-dihydroxy-3-butene with propylene. A sample of (R)-1,2-dihydroxy-3-butene (94% ee, 158 mg, 1.8 mmol) and $Cl_2Ru=CHPh[P(Cy_3)]_2$ (30 mg, 0.036 mmol, 2.0 mol %) were placed in a 150 mL glass pressure bottle (Fisher-Porter® reaction flask) and dissolved in dry dichloromethane (5 mL). The solution was degassed, pressurized with 50 psig of propylene and heated to 45° C. After 21 hours, heating was stopped and the pressure released. Reactants and products were analyzed by chiral GC as described above. The product showed a mixture of trans-1,2-dihydroxy-3-pentene enantiomers (confirmed by GC/MS) at 10.82 and 10.95 min. in a ratio of 1.00:71.94 corresponding to a 97.2% ee of the major isomer, assumed to be or the R configuration based on the identity of the reactant diol. Only a single peak of the pair associated with the cis-enantiomers at 11.97 minutes was detected, yielding a trans/cis integration ratio of 13.7.

Example 4

Hydrogenation of 1,2-dihydroxy-3-butene. 1,2-Dihydroxy-3-butene (105 mg, 1.2 mmol) and 5% Pd/C (127 mg, 0.060 mmol Pd) were mixed with 10 mL absolute ethanol. The mixture was degassed and $H_2$ (3.5 barg, approximately 50 psig) was added. After stirring for 16 h at ambient temperature the pressure was released. Pd/C was filtered off and solvent was removed in vacuo leaving a light yellow oil (40 mg, 0.44 mmol, 37% yield). $^1$H NMR analysis of the product indicates 1,2-dihydroxybutane. $^1$H NMR (CDCl$_3$) δ 3.65 (m, 2H), 3.45 (m, 1H), 1.80 (br s, 2H), 1.45 (m, 2 H), 0.98 (t, 3H).

Example 5

Cross-Metathesis of 4-vinyl-1,3-dioxolan-2-one (vinyl ethylene carbonate, VEC) with 1-pentene. VEC (205 mg, 1.79 mmol) and 1-pentene (379 mg, 5.4 mmol) were dissolved in dry dichloromethane (10 mL). The solution was degassed and heated to reflux. Upon reaching reflux, a solution of Cl2Ru=CHPh[P(Cy3)]2 (30 mg, 0.036 mmol, 2.0 mol %) in dry, degassed dichloromethane (10 mL) was added. Within 1 hour the solution changed color from purple to red-brown. After 16 hours, heating was stopped and solvent was removed in vacuo leaving a brown oil. 1H NMR spectroscopy shows both unreacted VEC and cross metathesis product in a 0.8:1 ratio indicating a 56% yield of 3-(pent-1-enyl)ethylenecarbonate. 1H NMR (CDCl3) □ 5.95 (m, 1H), 5.53 (m, 1H), 5.09 (q, 1 H), 4.56 (t, 1H), 4.12 (t, 1H), 2.10 (q, 2H), 1.44 (m, 2H), 0.92 (t, 3H).

Comparative Example 4

Self-metathesis of VEC. VEC (205 mg, 1.8 mmol) and $(PCy_3)_2Cl_2Ru=CHPh$ (30 mg, 0.036 mmol, 2.0 mol %) were dissolved in dry d$_2$-dichloromethane (5 ml). The solution was degassed and heated to 40° C. After 18 hours heating was stopped. $^1$H NMR analysis of the solution showed a small amount of internal olefin corresponds to 5% self-metathesis product

Comparative Example 5

Cross-metathesis of EpB with 1-pentene. EpB (70 mg, 1.0 mmol) and 1-pentene (701 mg, 10.0 mmol) were dissolved in dry dichloromethane (5 mL). The solution was degassed and heated to reflux. Upon reaching reflux, a solution of $(PCy_3)_2Cl_2Ru=CHPh$ (17 mg, 0.02 mmol, 2.0 mol %) in dry, degassed dichloromethane (5 mL) was added. The solution changed color quickly from purple to orange-brown. Heating was stopped after 19 h and the solution was analyzed by GC, which showed only unreacted EpB and 1-pentene along with some less abundant, unidentified products.

We claim:

1. Process for the preparation of a compound having the formula:

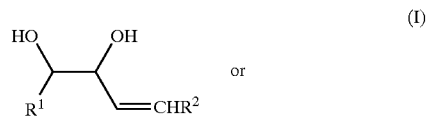

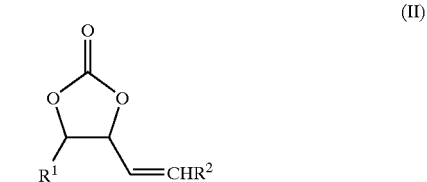

which comprises contacting a first olefin selected from α,β-dihydroxyalkenes having the formula:

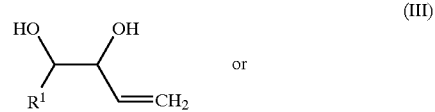

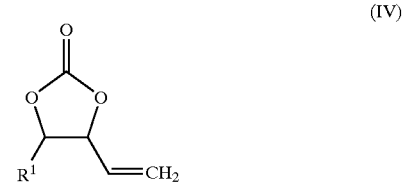

and at least one olefin having the formula $H_2C=CHR^2$ (V) or $R^2HC=CHR^2$ (VI) or a cycloalkene (VII) in the presence of an olefin metathesis catalyst under olefin metathesis conditions of pressure and temperature wherein $R^1$ is hydrogen, a $C_1$ to $C_{10}$, substituted or unsubstituted, straight or branched chain alkyl radical; a $C_2$ to $C_{10}$, substituted or unsubstituted, straight or branched chain alkenyl radical; a $C_3$ to $C_{10}$, substituted or unsubstituted cycloalkyl or cycloalkenyl radical; a $C_6$ to $C_{10}$, substituted or unsubstituted aryl radical; or a $C_4$ to $C_{10}$, substituted or unsubstituted heterocyclic radical containing from 1 to 3 heteroatoms selected from oxygen and sulfur;

$R^2$ each is $C_1$ to $C_{10}$, substituted or unsubstituted, straight or branched chain alkyl radical; $C_2$ to $C_{10}$, substituted or unsubstituted, straight or branched chain alkenyl radical; $C_3$ to $C_{10}$, substituted or unsubstituted cycloalkyl or cycloalkenyl radical; $C_6$ to $C_{10}$, substituted or unsubstituted aryl radical; or $C_4$ to $C_{10}$, substituted or unsubstituted heterocyclic radical containing from 1 to 3 heteroatoms selected from oxygen and sulfur; and cycloalkene (VII) is selected from the group consisting of substituted or unsubstituted cyclobutenes, cyclopentenes, cyclopentadienes, cyclohexenes, cycloheptenes, and cyclooctenes.

2. Process according to claim 1 wherein the olefin metathesis catalyst is a ruthenium or osmium alkylidene catalyst having the formula $MX_2[=CHR^3]L^1L^2$ wherein M is ruthenium or osmium, X is a halogen atom or pseudohalogen group such as carboxylate or alkoxide; $R^3$ is hydrogen, alkyl, cycloalkyl, vinyl, aryl or aralkyl; $L^1$ and $L^2$ are the same or different metal ligands selected from the group consisting of phosphines having the formula $P(R^4)_3$, wherein $R^4$ is alkyl, cycloalkyl, aryl, or aralkyl; phosphites having the formula $P(OR^4)_3$, wherein $R^4$ is alkyl, cycloalkyl, aryl, or aralkyl; alkenes, cycloalkenes, alkynes, nitric oxide, imines, imidazoylidenes and dihydroimidazoylidenes; and the process is carried out at a temperature of about 0 to about 60° C.

3. Process according to claim 1 for the preparation of a compound having the formula:

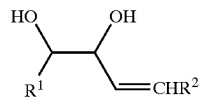

(I)

which comprises contacting an α,β-dihydroxyalkene having the formula:

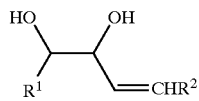

(III)

with an olefin having the formula $H_2C=CHR^2$ (V) or $R^2HC=CHR^2$ (VI) or a cycloalkene (VII) at a temperature of about 0° C. to about 60° C. in the presence of a ruthenium alkylidene olefin metathesis catalyst having the formula $RuX_2[=CHR^3]L^1L^2$ wherein X is a halogen atom;

$R^1$ is hydrogen, methyl, vinyl or phenyl;

$R^2$ is methyl, ethyl, propyl, butyl pentyl, vinyl or phenyl;

$R^3$ is hydrogen, alkyl, or aryl; and $L^1$ and $L^2$ are the same or different ruthenium ligands selected from the group consisting of phosphines having the formula $P(R^4)_3$ wherein $R^4$ is alkyl, cycloalkyl, aryl, or aralkyl; phosphites having the formula $P(OR^4)_3$ wherein $R^4$ is alkyl, cycloalkyl, aryl, or aralkyl; alkenes, cycloalkenes, alkynes, nitric oxide, imines, imidazoylidenes and dihydroimidazoylidenes.

4. Process according to claim 3 wherein the olefin metathesis catalyst is a ruthenium alkylidene phosphine catalyst having the formula $RuCl_2[=CHPh][P(Cy)_3]L^1$ wherein Cy is cyclohexyl, Ph is phenyl, and $L^1$ is $P(Cy)_3$ or 1,3-bis-(2,4,6-trimethylphenyl)-2-imidazolidinylidene.

5. Process for the preparation of an enantiomerically enriched compound having the formula:

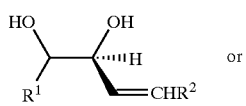

(I-A)

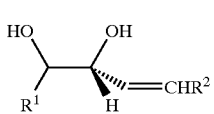

(I-B)

which comprises contacting an enantiomerically enriched α,β-dihydroxyalkene having the formula:

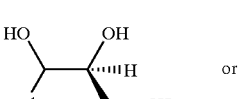

(III-A)

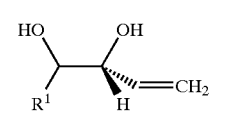

(III-B)

and at least one olefin selected from olefins having the formula $H_2C=CHR^2$ (V) or $R^2HC=CHR^2$ (VI) or a cycloalkene (VII) in the presence of an olefin metathesis catalyst under olefin metathesis conditions of pressure and temperature wherein $R^1$ is hydrogen, a $C_1$ to $C_{10}$, substituted or unsubstituted, straight or branched chain alkyl radical; a $C_2$ to $C_{10}$, substituted or unsubstituted, straight or branched chain alkenyl radical; a $C_3$ to $C_{10}$, substituted or unsubstituted cycloalkyl or cycloalkenyl radical; a $C_6$ to $C_{10}$, substituted or unsubstituted aryl radical; or a $C_4$ to $C_{10}$, substituted or unsubstituted heterocylic radical containing from 1 to 3 heteroatoms selected from oxygen and sulfur;

$R^2$ each is $C_1$ to $C_{10}$, substituted or unsubstituted, straight or branched chain alkyl radical; $C_2$ to $C_{10}$, substituted or unsubstituted, straight or branched chain alkenyl radical; $C_3$ to $C_{10}$, substituted or unsubstituted cycloalkyl or cycloalkenyl radical; $C_6$ to $C_{10}$, substituted or unsubstituted aryl radical; or $C_4$ to $C_{10}$, substituted or unsubstituted heterocylic radical containing from 1 to 3 heteroatoms selected from oxygen and sulfur; and cycloalkene (VII) is selected from the group consisting of substituted or unsubstituted cyclobutenes, cyclopentenes, cyclopentadienes, cyclohexenes, cycloheptenes, and cyclooctenes.

6. Process according to claim 5 wherein the olefin metathesis catalyst is a ruthenium or osmium alkylidene catalyst having the formula $MX_2[=CHR^3]L^1L^2$ wherein M is ruthenium or osmium, X is a halogen atom or pseudohalogen group such as carboxylate or alkoxide; $R^3$ is hydrogen, alkyl, cycloalkyl, aryl or aralkyl; $L^1$ and $L^2$ are the same or different metal ligands selected from the group consisting of phosphines having the formula $P(R^4)_3$, wherein $R^4$ is alkyl, cycloalkyl, aryl, or aralkyl; phosphites having the formula $P(OR^4)_3$, wherein $R^4$ is alkyl, cycloalkyl, aryl, or aralkyl; alkenes, cycloalkenes, alkynes, nitric oxide, imines, imidazoylidenes and dihydroimidazoylidenes; and the process is carried out at a temperature of about 0 to about 60° C.

7. Process according to claim 6 wherein the olefin metathesis catalyst is a ruthenium alkylidene phosphine catalyst having the formula $RuCl_2[=CHPh][P(Cy)_3]L^1$ wherein Cy is cyclohexyl, Ph is phenyl, and $L^1$ is $P(Cy)_3$ or 1,3-bis-(2,4,6-trimethylphenyl)-2-imidazolidinylidene; and the process is carried out at a temperature of about 0 up to 60° C.

8. Process according to claim 7 wherein $R^1$ is hydrogen, methyl, phenyl, or vinyl; and $R^2$ is propene or butene.

9. Process according to claim 5 for the preparation of an enantiomerically enriched product compound having the formula:

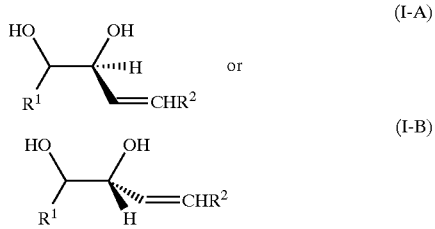

which comprises contacting an enantiomerically enriched α,β-dihydroxyalkene having the formula:

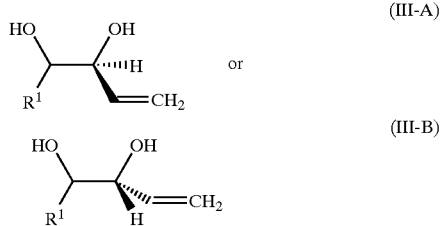

with an olefin having the formula $H_2C=CHR^2$ (V) or $R^2HC=CHR^2$ (VI) or a cycloalkene (VII) at a temperature of about 0 to about 60° C in the presence of an olefin metathesis ruthenium or osmium alkylidene catalyst having the formula $MX_2[=CHR^3]L^1L^2$; wherein M is ruthenium or osmium;

X is a halogen atom;

$R^1$ is hydrogen, methyl, vinyl, or phenyl;

$R^2$ is methyl, ethyl, propyl, butyl, pentyl, vinyl or phenyl;

$R^3$ is hydrogen, alkyl, or aryl; and $L^1$ and $L^2$ are the same or different metal ligands selected from the group consisting of phosphines having the formula $P(R^4)_3$, wherein $R^4$ is alkyl, cycloalkyl, aryl, or aralkyl; phosphites having the formula $P(OR^4)_3$, wherein $R^4$ is alkyl, cycloalkyl, aryl, or aralkyl; alkenes, cycloalkenes, alkynes, nitric oxide, imines, imidazoylidenes and dihydroimidazoylidenes; and wherein the product compound has substantially the same enantiomeric composition as the (α,β-dihydroxyalkene reactant.

10. Process according to claim 8 wherein the olefin metathesis catalyst is a ruthenium alkylidene phosphine catalyst having the formula $RuCl_2[=CHPh][P(Cy)_3]L^1$ wherein Cy is cyclohexyl, Ph is phenyl, and $L^1$ is $P(Cy)_3$ or 1,3-bis-(2,4,6-trimethylphenyl)-2-imidazolidinylidene.

11. Process for the preparation of a compound having the formula:

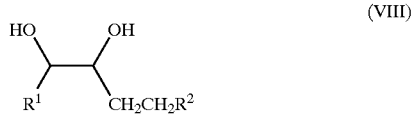

which comprises the steps of:
(1) contacting an α,β-dihydroxyalkene having the formula:

with at least one olefin having the formula $H_2C=CHR^2$ (V) or $R^2HC=CHR^2$ (VI) or a cycloalkene (VII) in the presence of an olefin metathesis catalyst under olefin metathesis conditions of pressure and temperature to produce a compound having the formula:

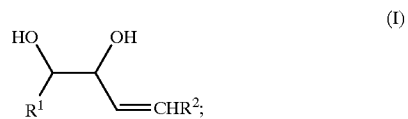

and
(2) hydrogenating compound (I) produced in step (1) to obtain a compound having the formula of VIII wherein $R^1$ is hydrogen, a $C_1$ to $C_{10}$, substituted or unsubstituted, straight or branched chain alkyl radical; a $C_2$ to $C_{10}$, substituted or unsubstituted, straight or branched chain alkenyl radical; a $C_3$ to $C_{10}$, substituted or unsubstituted cycloalkyl or cycloalkenyl radical; a $C_6$ to $C_{10}$, substituted or unsubstituted aryl radical; or a $C_4$ to $C_{10}$, substituted or unsubstituted heterocylic radical containing from 1 to 3 heteroatoms selected from oxygen and sulfur;

$R^2$ each is $C_1$ to $C_{10}$, substituted or unsubstituted, straight or branched chain alkyl radical; $C_2$ to $C_{10}$, substituted or unsubstituted, straight or branched chain alkenyl radical; $C_3$ to $C_{10}$, substituted or unsubstituted cycloalkyl or cycloalkenyl radical; $C_6$ to $C_{10}$, substituted or unsubstituted aryl radical; or $C_4$ to $C_{10}$, substituted or unsubstituted heterocylic radical containing from 1 to 3 heteroatoms selected from oxygen and sulfur; and cycloalkene (VII) is selected from the group consisting of substituted or unsubstituted cyclobutenes, cyclopentenes, cyclopentadienes, cyclohexenes, cycloheptenes, and cyclooctenes.

12. Process according to claim 11 wherein the olefin metathesis catalyst is a ruthenium or osmium alkylidene catalyst and has the formula $MX_2[=CHR^3]L^1L^2$ wherein M is ruthenium or osmium, X is a halogen atom or pseudohalogen group such as carboxylate or alkoxide; $R^3$ is hydrogen, alkyl, cycloalkyl, aryl or aralkyl; and $L^1$ and $L^2$ are the same or different metal ligands selected from the group consisting of phosphines having the formula $P(R^4)_3$, wherein $R^4$ is alkyl, cycloalkyl, aryl, or aralkyl; phosphites having the formula $P(OR^4)_3$, wherein $R^4$ is alkyl, cycloalkyl, aryl, or aralkyl; alkenes, cycloalkenes, alkynes, nitric oxide, imines, imidazoylidenes and dihydroimidazoylidenes; and the process is carried out at a temperature of about 0 to about 60° C.

13. Process according to claim 12 wherein the olefin metathesis catalyst is a ruthenium alkylidene phosphine catalyst having the formula $RuX_2[=CHR^3][P(R^4)_3]L^1$ wherein X is a halogen atom; $R^3$ is hydrogen, alkyl, or aryl; $R^4$ is alkyl, cycloalkyl, aryl, or aralkyl; $L^1$ is $P(R^4)_3$, imidazoylidene or dihydroimidazoylidene and the process is carried out at a temperature of about 0 to about 60° C.

14. Process according to claim 13 wherein the hydrogenation step (2) is carried out in the presence of a hydrogenation catalyst comprising one or more metals or metal compounds selected from Groups 7 to 11 of the Periodic Table of the Elements.

15. Process according to claim 14 wherein the hydrogenation catalyst is selected from the group consisting of Pd/C, Pt/C, Re/C, Cu/C, Cu/SiO$_2$, Ni/C, Raney nickel, Raney cobalt, and combinations thereof.

16. Process according to claim 14 wherein the hydrogenation catalyst is the olefin metathesis catalyst of claim 12.

17. Process for the preparation of an enantiomerically enriched diol compound having the formula:

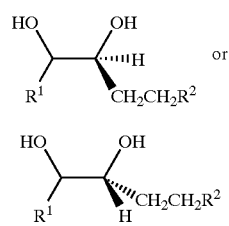

(VIII-A) or (VIII-B)

which comprises the steps of:

(1) contacting an enatiomerically enriched α,β-dihydroxyalkene having the formula:

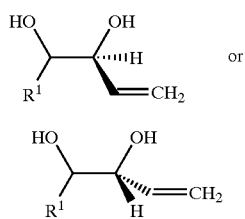

(III-A) or (III-B)

with at least one olefin having the formula H$_2$C=CHR$^2$ (V) or R$^2$HC=CHR$^2$ (VI) or a cycloalkene (VII) in the presence of an olefin metathesis catalyst under olefin metathesis conditions of pressure and temperature to produce a compound having the formula:

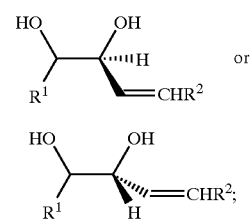

(I-A) or (I-B)

and (2) hydrogenating compound I-A or I-B produced in step (1) to obtain a compound having the formula VIII-A or VIII-B wherein $R^1$ is hydrogen, a $C_1$ to $C_{10}$, substituted or unsubstituted, straight or branched chain alkyl radical; a $C_2$ to $C_{10}$, substituted or unsubstituted, straight or branched chain alkenyl radical; a $C_3$ to $C_{10}$, substituted or unsubstituted cycloalkyl or cycloalkenyl radical; a $C_6$ to $C_{10}$, substituted or unsubstituted aryl radical; or a $C_4$ to $C_{10}$, substituted or unsubstituted heterocylic radical containing from 1 to 3 heteroatoms selected from oxygen and sulfur;

$R^2$ each is $C_1$ to $C_{10}$, substituted or unsubstituted, straight or branched chain alkyl radical; $C_2$ to $C_{10}$, substituted or unsubstituted, straight or branched chain alkenyl radical; $C_3$ to $C_{10}$, substituted or unsubstituted cycloalkyl or cycloalkenyl radical; $C_6$ to $C_{10}$, substituted or unsubstituted aryl radical; or $C_4$ to $C_{10}$, substituted or unsubstituted heterocylic radical containing from 1 to 3 heteroatoms selected from oxygen and sulfur; and cycloalkene (VII) is selected from the group consisting of substituted or unsubstituted cyclobutenes, cyclopentenes, cyclopentadienes, cyclohexenes, cycloheptenes, and cyclooctenes.

18. Process according to claim 17 wherein the olefin metathesis catalyst is a ruthenium or osmium alkylidene catalyst and has the formula MX$_2$[=CHR$^3$]L$^1$L$^2$ wherein M is ruthenium or osmium, X is a halogen atom or pseudohalogen group such as carboxylate or alkoxide; R$^3$ is hydrogen, alkyl, cycloalkyl, aryl or aralkyl; and L$^1$ and L$^2$ are the same or different metal ligands selected from the group consisting of phosphines having the formula P(R$^4$)$_3$, wherein R$^4$ is alkyl, cycloalkyl, aryl, or aralkyl; phosphites having the formula P(OR$^4$)$_3$, wherein R$^4$ is alkyl, cycloalkyl, aryl, or aralkyl; alkenes, cycloalkenes, alkynes, nitric oxide, imines, imidazoylidenes and dihydroimidazoylidenes; and the process is carried out at a temperature of about 0 to about 60° C.

19. Process according to claim 18 wherein the olefin metathesis catalyst is a ruthenium phosphine catalyst having the formula RuX$_2$[=CHR$^3$]—[P(R$^4$)$_3$]L$^1$ wherein X is a halogen atom; R$^3$ is hydrogen, alkyl, or aryl; and R$^4$ is alkyl, cycloalkyl, aryl, or aralkyl; L$^1$ is P(R$^4$)$_3$, imidazoylidene or dihydroimidazoylidene; and the process is carried out at a temperature of about 0 to about 60° C.

20. Process according to claim 17 wherein the hydrogenation step (2) is carried out in the presence of a hydrogenation catalyst comprising one or more metals or metal compounds selected from Groups 7 to 11 of the Periodic Table of the Elements.

21. Process according to claim 20 wherein the hydrogenation catalyst is one or more catalysts selected from the group consisting of Pd/C, Pt/C, Re/C, Cu/C, Cu/SiO$_2$, Ni/C, Raney nickel, Raney cobalt, and phosphine complexes of metals from Groups 8 to 10 of the Periodic Table of the Elements.

22. Process according to claim 20 wherein the hydrogenation catalyst is the olefin metathesis catalyst of claim 18.

* * * * *

UNITED STATES PATENT AND TRADEMARK OFFICE
CERTIFICATE OF CORRECTION

PATENT NO.  : 7,002,049 B2
DATED       : February 21, 2006
INVENTOR(S) : Hembre et al.

It is certified that error appears in the above-identified patent and that said Letters Patent is hereby corrected as shown below:

<u>Column 20,</u>
Lines 15 to 28 reads " 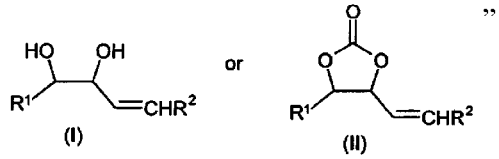 "

should read -- 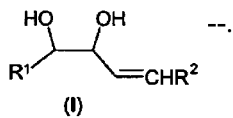 --.

Lines 33 to 43 reads " 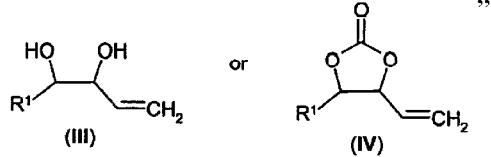 "

should read -- 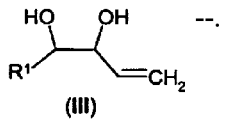 --.

UNITED STATES PATENT AND TRADEMARK OFFICE
CERTIFICATE OF CORRECTION

PATENT NO. : 7,002,049 B2
DATED : February 21, 2006
INVENTOR(S) : Hembre et al.

It is certified that error appears in the above-identified patent and that said Letters Patent is hereby corrected as shown below:

Column 21,
Lines 30 to 35, reads " 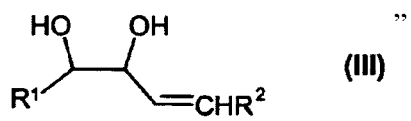 "

should read -- 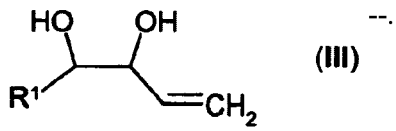 --.

Signed and Sealed this

Thirteenth Day of June, 2006

JON W. DUDAS
*Director of the United States Patent and Trademark Office*